US006682753B2

(12) United States Patent
Alexi

(10) Patent No.: US 6,682,753 B2
(45) Date of Patent: Jan. 27, 2004

(54) METHODS FOR PROMOTING WEIGHT GAIN USING GPE-RELATED COMPOUNDS

(75) Inventor: Tajrena Alexi, Auckland (NZ)

(73) Assignee: NeuronZ Limited, Auckland (NZ)

(*) Notice: Subject to any disclaimer, the term of this patent is extended or adjusted under 35 U.S.C. 154(b) by 0 days.

(21) Appl. No.: 10/099,134

(22) Filed: Mar. 13, 2002

(65) Prior Publication Data

US 2002/0151522 A1 Oct. 17, 2002

Related U.S. Application Data

(60) Provisional application No. 60/278,562, filed on Mar. 23, 2001.

(51) Int. Cl.[7] .................... A61K 38/04; A61K 138/00
(52) U.S. Cl. .................... 424/422; 424/423; 424/489
(58) Field of Search ................ 424/439, 422, 424/423, 489; 514/18, 19

(56) References Cited

U.S. PATENT DOCUMENTS

| 5,714,460 A | * | 2/1998 | Gluckman et al. ........... 514/3 |
| 6,187,906 B1 | * | 2/2001 | Gluckman et al. ........... 530/331 |
| 6,294,585 B1 | * | 9/2001 | Brown ........................ 514/729 |
| 6,365,573 B1 | * | 4/2002 | Gluckman et al. ........... 514/18 |
| 6,617,311 B1 | * | 9/2003 | Gluckman et al. ........... 514/19 |

FOREIGN PATENT DOCUMENTS

| EP | 0 366 638 A2 | 5/1990 |
| WO | WO 98/14202 AI | 4/1998 |

OTHER PUBLICATIONS

Ballard, F.J., et al., "Des (1–3) IGF–I: a truncated form of insuling–like growth factor–I", Int. J. Biochem. Cell Biol. 1996, vol. 28, No. 10, pp. 1085–1087.

* cited by examiner

Primary Examiner—Thurman K. Page
Assistant Examiner—Rachel M. Bennett
(74) Attorney, Agent, or Firm—Fliesler Dubb Meyer & Lovejoy LLP

(57) ABSTRACT

Weight gain in a mammal, especially a human, having a condition that leads to decreased weight gain or weight loss, such as AIDS, brain trauma, a chronic neurodegenerative disease such as Alzheimer's disease, Parkinson's disease, Huntington's disease, or multiple sclerosis, or other condition, is promoted by increasing the effective concentration of a GPE-related compound (GPE or a GPE analog) in the central nervous system of the mammal. This increase may be achieved by administration to the mammal of an effective amount of a GPE-related compound, a prodrug thereof, or an implant containing cells that express the GPE-related compound or prodrug.

24 Claims, 1 Drawing Sheet

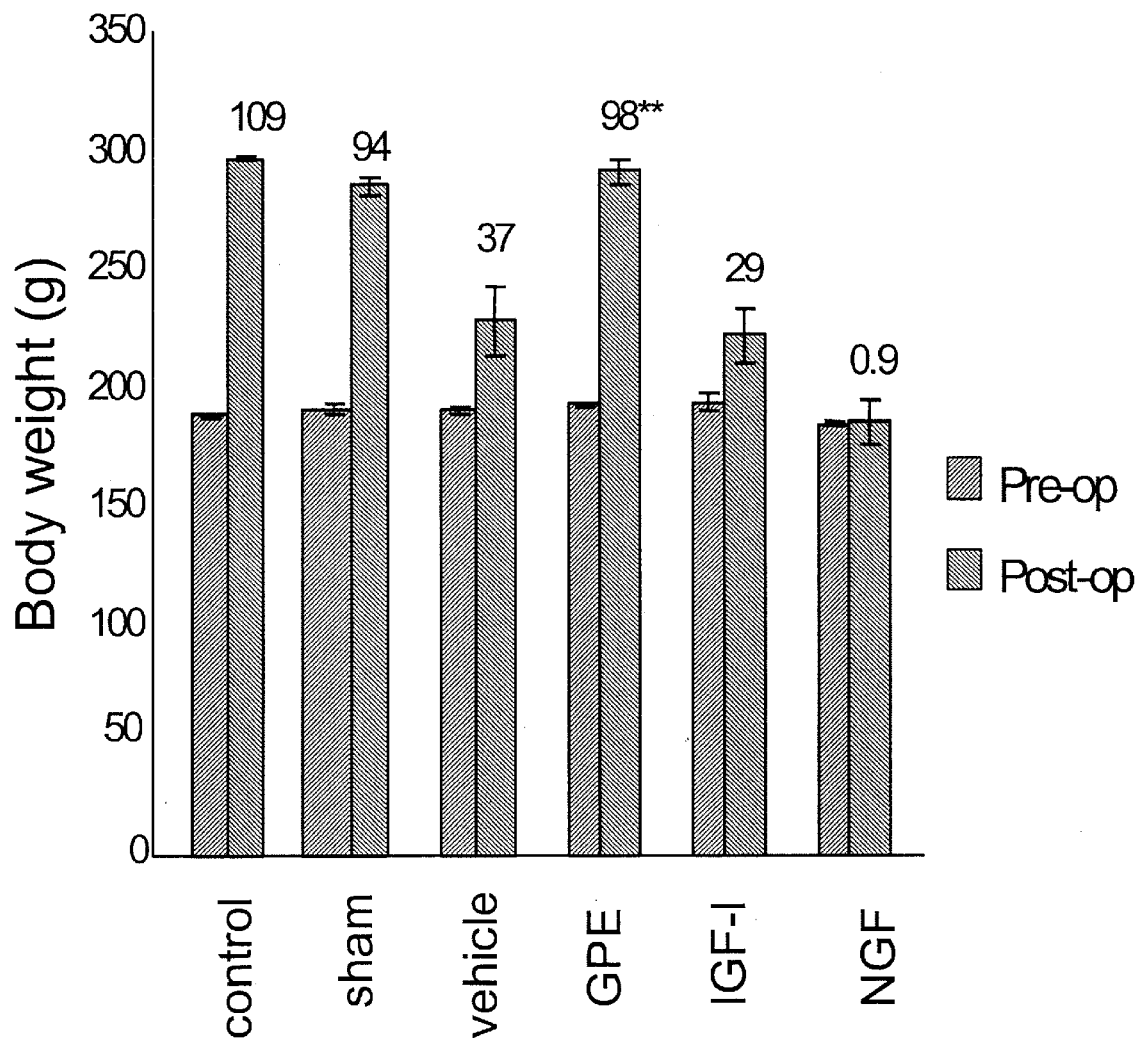

METHODS FOR PROMOTING WEIGHT GAIN USING GPE-RELATED COMPOUNDS

CROSS REFERENCE TO RELATED APPLICATION

This application claims the priority under 35 USC 119(e) of U.S. Provisional Application No. 60/278,562, filed Mar. 23, 2001, the disclosure of which is incorporated by reference into this application.

BACKGROUND OF THE INVENTION

1. Field of the Invention

This invention relates to methods of promoting weight gain.

2. Description of the Related Art

Weight loss after head injury is a common side effect (Pepe et al. (1999), The metabolic response to acute traumatic brain injury and implications for nutritional support, *Journal of Head Trauma and Rehabilitation*, 5: 462–474; Borzotta et al. (1994), Enteral versus parenteral nutrition after severe closed head injury, *Journal of Trauma*, 37(3): 459–468; Flakoll et al. (1995), Protein and glucose metabolism during isolated closed-head injury, *American Journal of Physiology*, 269(4Pt1): E636–E641). There are also no treatments currently available to prevent the cell death that occurs in the brain as a consequence of head injury.

Similarly, weight loss is a common symptom associated with chronic neurological diseases, such as Alzheimer's disease, Parkinson's disease, Huntington's disease and multiple sclerosis. Treatments available at present for such chronic neurological diseases only target symptoms. No drugs are currently available to intervene in the disease process.

Various growth factors have been shown to be neuroprotective and therefore have utility in the prevention or inhibition of neural cell death (AU 700838; WO 95/17204; U.S. Pat. Nos. 5,714,460; 5861373; EP 625050; WO 99/15912; WO 00/13650). However, it has been shown in human patients that growth factors can cause weight loss. Nerve growth factor (NGF) administered intracerebroventricularly to patients with Alzheimer's disease can cause marked weight reduction (Eriksdotter et al. (1998), Intracerebroventricular infusion of nerve growth factor in three patients with Alzheimer's disease, *Dementia and Geriatric Cognitive Disorders*, 9(5): 246–257).

Weight loss following administration of growth factors to the brain has also been found to occur in monkeys (Miyoshi et al. (1997), Glial cell line-derived neurotrophic factor-Levodopa interactions and reduction of side effects in Parkinsonian monkeys, *Annals of Neurology*, 42: 208–214). Similarly, the following growth factors have been shown to either decrease normal body weight gain or cause weight loss when infused in the brain of adult rats following either partial or full lesions to an area of the brain, such as a partial fimbria-fornix transection: brain-derived neurotrophic factor (BDNF) (Lapchak et al. (1992), BDNF and NGF treatment in lesioned rats: effects on cholinergic function and weight gain, *NeuroReport*, 3: 405–408; Altar et al. (1994), Efficacy of brain-derived neurotrophic factor and neurotrophin-3 on neurochemical and behavioral deficits associated with partial nigrostriatal dopamine lesions, *Journal of Neurochemistry*, 63: 1021–1032), basic fibroblast growth factor (bFGF) (Araujo et al. (1993), Effects of chronic basic fibroblast growth factor administration to rats with partial fimbrial transections on presynaptic cholinergic parameters and muscarinic receptors in the hippocampus: comparison with nerve growth factor, *Journal of Neurochemistry*, 61: 889–910; Williams et al. (1996), Glial cell line-derived neurotrophic factor sustains axotomized basal forebrain cholinergic neurons in vivo: dose response comparison to nerve growth factor and brain-derived neurotrophic factor, *Journal of Pharmacology and Experimental Therapeutics*, 277: 1140–1151), glial-derived neurotrophic factor (GDNF) (Giehl et al. (1998), Infusion of GDNF into the cerebral spinal fluid through two different routes: effects on body weight and corticospinal neuron survival, *NeuroReport*, 9: 2809–2813; Williams et al. (1996), Glial cell line-derived neurotrophic factor sustains axotomized basal forebrain cholinergic neurons in vivo: dose response comparison to nerve growth factor and brain-derived neurotrophic factor, *Journal of Pharmacology and Experimental Therapeutics*, 277: 1140–1151) and nerve growth factor (NGF) (Winkler et al. (1995), Effects of nerve growth factor treatment on rats with lesions of the nucleus basalis magnocellularis produced by ibotenic acid, quisqualic acid, and AMPA, *Experimental Neurology*, 136: 234–250).

Furthermore, BDNF, GDNF and NGF administered to the brain of normal, unlesioned rats have been shown to cause weight loss (Pelleymounter et al. (1995), Characteristics of BDNF-induced weight loss, *Experimental Neurology*, 131: 229–238; Martin et al. (1996), Intranigral or intrastriatal injections of GDNF: effects on monoamine levels and behavior in animals, *European Journal of Pharmacology*, 317: 247–256; Williams (1991), Hypophagia is induced by intracerebroventricular administration of nerve growth factor, *Experimental Neurology*, 113: 31–37).

In contrast, insulin-like growth factor I (IGF-I) has been shown to cause weight gain in humans when administered intravenously after moderate to severe head injury (Hatton et al. (1997), Intravenous insulin-like growth factor-I (IGF-I) in moderate-to-severe head injury: a phase II safety and efficacy trial, *Journal of Neurosurgery*, 86(5): 779–786). Similarly, IGF-I has been shown to cause weight gain when administered into the brain following a transient ischemia to the forebrain in adult rats (Zhu et al. (1994), Intraventricular administration of insulin and IGF-1 in transient forebrain ischemia, *Journal of Cerebral Blood Flow and Metabolism*, 14(2): 237–242).

GPE is the tripeptide glycyl-L-prolyl-L-glutamic acid (gly-pro-glu). GPE and its dipeptide analogs GP (glycl-L-proline, gly-pro) and PE (L-prolyl-L-glutarnic acid, pro-glu) were first disclosed in EP 366638. The suggestion has been made in EP 366638 that GPE has neuromodulatory properties. GPE has also been established as having neuroprotective properties and therefore has utility in the prevention or inhibition of neuronal and glial cell death (WO 95/17204, AU 700838). GPE has also been established as having neuromodulatory properties and therefore has utility in increasing the effective amount of choline acetyltransferase (ChAT), nitric oxide synthase (NOS), glutamic acid decarboxylase (GAD) (WO 98/14202) and tyrosine hydroxylase (WO 99/65509) in the brain.

SUMMARY OF THE INVENTION

This invention is a method of promoting weight gain in a mammal, especially a human, having a condition that leads to decreased weight gain or weight loss, comprising increasing the effective concentration of a GPE-related compound in the central nervous system of the mammal. This increase may be achieved by administration to the mammal of an effective amount of a GPE-related compound, a prodrug thereof, or an implant containing cells that express the GPE-related compound or prodrug.

In another aspect, this invention is the use of a GPE-related compound, a prodrug thereof, or an implant containing cells that express the GPE-related compound or prodrug in the manufacture of a medicament for promoting weight gain in a mammal having a condition that leads to decreased weight gain or weight loss; and the medicament so made.

DESCRIPTION OF THE DRAWING

The FIGURE is a graph showing the pre-operative and post-operative weights of rats following no surgery; sham surgery and treatment; or surgery and treatment with vehicle, GPE, IGF-1, or NGF during surgery and then once daily for 14 days.

DETAILED DESCRIPTION OF THE INVENTION

Definitions

A "GPE-related compound" is GPE or a GPE analog.

A "GPE analog" is a small peptide (not more than 5 amino acids) or peptidomimetic (a compound where one or more of the amide bonds of such a peptide is replaced by a non-amide bond) that is capable of effective binding to mammalian central nervous system GPE receptors. Preferred GPE analogs are those capable of effectively promoting a weight gain substantially equivalent to that promoted by GPE itself. GPE analogs include the dipeptides gly-pro (GP) and pro-glu (PE), GPE amide, GPE stearate, gly-pro-D-glutamate (GP-D-E), gly-pro-thr (GPT), gly-glu-pro (GEP), glu-gly-pro (EGP), and glu-pro-gly (EPG).

A "prodrug" of a GPE-related compound is a compound comprising the GPE-related compound and a carrier linked to the GPE-related compound by chemical bond(s) that are cleaved by biological processes within a mammal when the prodrug is administered to the mammal, such as by the action of enzyme(s) present within the mammal. Prodrugs include, for example, esters of the GPE-related compound, such as the 1-[(ethoxycarbonyl)oxy]ethyl ester, and polypeptides that, when cleaved by a mammalian enzyme, yield the GPE-related compound. Suitable enzymes include an acid protease that generates des-(1–3) IGF-1 and GPE from IGF-1 (Yamamoto et al. (1994), Generation of des (1–3) insulin-like growth factor-I in serum by an acid protease, *Endocrinology*, 135(6): 2432–2439), proprotein and prohormone convertases (Seidah et al. (1999) Proprotein and prohormone convertases: a family of subtilases generating diverse bioactive polypeptides, *Brain Research* 848: 45–62), serum proteases, trypsin (in a calcium/magnesium-free solution), cathepsin-D, and pepstatin-A.

"Promoting weight gain in a mammal having a condition that leads to decreased weight gain or weight loss" by increasing the effective concentration of a GPE-related compound in the central nervous system of the mammal includes both the promotion of weight gain beyond that weight gain that would be incurred without such increase in effective concentration of the GPE-related compound, if such condition leads to decreased weight gain, and the reduction or prevention of that weight loss that would be incurred without such increase, if such condition leads to weight loss.

An "effective amount" of a GPE-related compound, prodrug, or implant is that amount of such compound, prodrug, or implant that, when administered to a mammal having a condition that leads to decreased weight gain or weight loss, produces an increase in effective concentration of a GPE-related compound in the central nervous system of the mammal sufficient to promote weight gain in that mammal.

Description and Preferred Embodiments

This invention is a method of promoting weight gain in a mammal having a condition that leads to decreased weight gain or weight loss, comprising increasing the effective concentration of a GPE-related compound in the central nervous system of the mammal.

Conditions suitable for the treatment of this invention include neural injury, neurological diseases, severe burns, severe trauma, chronic non-neurological diseases, chronic infections, chronic corticosteroid administration, AIDS, and the like. Neural injuries include acute brain injuries, traumatic brain injuries, closed head injuries, stroke, and the like. Neurological diseases include chronic neurodegenerative diseases such as Alzheimer's disease, Parkinson's disease, Huntington's disease, multiple sclerosis, and the like. The chronic corticosteroid administration may be associated with anti-neoplastic therapy, anti-inflammatory therapy, immunosuppression, and the like.

A particular advantage of the treatment of this invention in neural injury or neurodegenerative disease is that, in addition to promoting weight gain, the treatment is therapeutic for the rescue of neuronal and glial cells.

The preferred GPE-related compound is GPE.

The increase in the effective concentration of a GPE-related compound in the central nervous system of the mammal may be achieved by administration to the mammal of an effective amount of the GPE-related compound, a prodrug thereof, or an implant containing cells that express the GPE-related compound or prodrug. The administration may be either prophylactic (before such decreased weight gain or weight loss occurs), therapeutic (while such decreased weight gain or weight loss is occurring), or both.

The GPE-related compound or prodrug can be administered alone, or as is preferred, as a part of a pharmaceutical composition or medicament. In general, GPE compounds will be administered as pharmaceutical compositions by one of the following routes: directly to the central nervous system, oral, topical, systemic (e.g. transdermal, intranasal, or by suppository), parenteral (e.g. intramuscular, subcutaneous, or intravenous injection), by implantation and by infusion through such devices as osmotic pumps, transdermal patches and the like. Compositions may take the form of tablets, pills, capsules, semisolids, powders, sustained release formulation, solutions, suspensions, elixirs, aerosols or any other appropriate compositions; and comprise at least GPE-related compound or prodrug in combination with at least one pharmaceutically acceptable excipient. Suitable excipients are well known to persons of ordinary skill in the art, and they, and the methods of formulating the compositions, may be found in such standard references as Gennaro, ed. (2000), "Remington: The Science and Practice of Pharmacy", $20^{th}$ ed., Lippincott, Williams & Wilkins, Philadelphia Pa. Suitable liquid carriers, especially for injectable solutions, include water, aqueous saline solution, aqueous dextrose solution, and the like, with isotonic solutions being preferred for intravenous administration.

The GPE or other GPE-related compound, or prodrug can be administered directly to the central nervous system. This route of administration can involve, for example, lateral cerebroventricular injection, focal injection, or a surgically inserted shunt into the lateral cerebral ventricle.

An advantage of GPE and other GPE-related compounds is that they can be administered peripherally and have both peripheral and central nervous system effects. Thus, GPE and other GPE-related compounds and prodrugs need not be administered directly to the central nervous system in order to have effect in the central nervous system. Any peripheral route known in the art can be employed. Two particularly convenient peripheral administration routes are by subcutaneous injection (e.g. dissolved in 0.9% sodium chloride) and by oral administration (e.g., in a tablet or capsule).

GPE and other GPE-related compounds and prodrugs can also be administered by a sustained-release system. Suitable examples of sustained-release compositions include semi-permeable polymer matrices in the form of shaped articles, e.g. films, or microcapsules. Sustained-release matrices include polylactides (U.S. Pat. No. 3,773,919; EP 58481), copolymers of L-glutamic acid and γ-ethyl-L-glutamate (Sidman et al., (1983) Controlled release of macromolecules and pharmaceuticals from synthetic polypeptides based on glutamic acid, *Biopolymers*, 22: 547–556), poly(2-hydroxyethylmethacrylate) (Langer et al., (1981) Biocompatibility of polymeric delivery systems for macromolecules, *Journal of Biomedical Materials Research*, 15: 267–277) ethylene vinyl acetate (Langer et al., supra), or poly-D-(-)-3-hydroxybutyric acid (EP 133988). Sustained-release compositions also include liposomally entrapped compounds. Liposomes containing the compound are prepared by methods known per se: DE 3218121; Hwang et al., (1980) Hepatic uptake and degradation of unilamellar sphingomyelin/cholesterol liposomes: a kinetic study, *Proceedings of the National Academy of Sciences USA*, 77: 4030–4034); EP 52322; EP 36676; EP 88046; EP 143949; EP 142641; JP 83-118008; U.S. Pat. Nos. 4,485,045, 4,544,545; and EP 102324. Ordinarily, the liposomes are of the small (from about 20 to about 80 nm diameter) unilamellar type in which the lipid content is greater than about 30 mole percent cholesterol, the selected proportion being adjusted for the most efficacious therapy. Other sustained-release systems include implantable osmotic systems of the type described in U.S. Pat. No. 5,980,508. The GPE-related compounds and prodrugs may also be PEGylated to increase their lifetime in vivo, based on, e.g. the conjugate technology described in WO 95/32003. Mechanical devices providing sustained infusion, such as those commonly used for the delivery of insulin, may also be used.

The effective concentration of GPE or other GPE-related compounds can also be increased by the use of an implant which is or includes a stable expression cell line which is capable of expressing the GPE-related compound in an active form within the body, or more particularly the central nervous system of the patient (Martinez-Serrano et al. (1998), Ex vivo nerve growth factor gene transfer to the basal forebrain in presymptomatic middle-aged rats prevents the development of cholinergic neuron atrophy and cognitive impairment during aging, *Proceedings of the National Academy of Sciences USA*, 95: 1858–1863; Chen et al. (1995), Somatic gene transfer of NGF to the aged brain: behavioral and morphological amelioration, *Journal of Neuroscience*, 15(4): 2819–2825). Cells such as astrocytes (Yoshimoto et al. (1995), Astrocytes retrovirally transduced with BDNF elicit behavioural improvement in a rat model of Parkinson's disease, *Brain Research*, 691: 25–36), fibroblasts (Chen et al. (1995), Somatic gene transfer of NGF to the aged brain: behavioral and morphological amelioration, *Journal of Neuroscience*, 15(4): 2819–2825; Frim et al. (1994), Implanted fibroblasts genetically engineered to produce brain-derived neurotrophic factor prevent 1-methyl-4-phenylpyridinium toxicity to dopaminergic neurons in the rat, *Proceedings of the National Academy of Sciences USA*, 91: 5104–5108), HiB5 cells (Martinez-Serrano et al. (1998), Ex vivo nerve growth factor gene transfer to the basal forebrain in presymptomatic middle-aged rats prevents the development of cholinergic neuron atrophy and cognitive impairment during aging, *Proceedings of the National Academy of Sciences USA*, 95: 1858–1863), and baby hamster kidney cells (Tseng et al., (1997), GDNF reduces drug-induced rotational behavior after medial forebrain bundle transection by a mechanism not involving striatal dopamine, *Journal of Neuroscience*, 17(1): 325–333), either primary cells or cell lines, immortalized or not, and engineered to express the GPE-related compound may be implanted into the brain or elsewhere in the body, or encapsulated in biocompatible polymers, fibers or other materials and the cell-containing capsules then implanted into the brain or elsewhere in the body. Cells may be cultured in Dulbecco's Modified Eagle's Medium (DMEM) containing 10% fetal calf serum and 1% penicillin/streptomycin prior to encapsulation and/or implantation. Cells to be encapsulated may be suspended in a solution of 1:1 culture media: to 3% collagen at a density of 500,000 cells/$\mu$L. This cell suspension can then be encapsulated in capsules such as poly(ethersulfone) (PES) fibers from AKZO-Fiber Nobel AG, Wupperthal, Germany). Capsules are preferably cultured for 4 days before implantation.

Engineering cells to express a GPE-related compound in active form may be achieved through the use of an expression vector. For example, for GPE, multiple copies of any DNA sequence specific for the amino acids methionine/glycine/proline/glutamic acid and a stop codon are linked together, either with or without additional DNA sequences specific for a stop codon between each 4 amino acid sequence, to form a complete sequence of between 30–50 nucleotides. Note that the start codon will always be ATG, the codon for methionine, whereas the stop codon may be either TAA, TAG or TGA. This complete sequence comprises the expression vector for GPE. The expression vector as a whole will generally also include a promoter for the cell to be implanted, and may include selection markers and other DNA sequences common in the biotechnology field. This vector is then integrated into the genome of the cells to be implanted.

The calculation of the effective amount of GPE-related compound or prodrug to be administered will be dependent upon the route of administration and upon the nature of the condition which is to be treated, and will be routine to a persons of ordinary skill in the art. For a human, where the dose is administered centrally, a suitable dose range for GPE is between about 0.1 $\mu$g and about 400 $\mu$g per Kg of body weight per day; a preferred dose range is between about 0.5 $\mu$g/Kg/day and about 50 $\mu$g/Kg/day, and a more preferred dose range is from about 1 $\mu$g/Kg/day to about 25 $\mu$g/Kg/day. For peripheral administration, the doses are about 10-fold to 1000-fold higher; and suitable dose ranges will be readily determinable by comparing the activities of peripherally administered GPE with the activity of centrally-administered GPE in a suitable model and scaling the central GPE dose range above accordingly. Suitable dose ranges for other GPE-related compounds will be readily determinable by comparing the activities of the compounds with the activity of GPE in a suitable model and scaling the GPE dose range above accordingly; and suitable dose ranges for prodrugs and implants will be determinable in the same manner.

The GPE-related compound or prodrug can be obtained from a suitable commercial source. Alternatively, the GPE-related compound or prodrug can be directly synthesized by conventional methods, such as the stepwise solid phase synthesis method of Merrifield et al., (1963) *Journal of the*

*American Chemical Society*, 85: 2149–2156, or other appropriate methods known to those of ordinary skill in chemical/biochemical synthesis. Synthesis can also involve the use of commercially available peptide synthesizers such as the Applied Biosystems model 430A.

EXAMPLE 1

The following experimental protocol followed guidelines that were approved by the University of Auckland Animal Ethics Committee.

A group of male Wistar rats weighing 174–193 g (University of Auckland, Animal Resources Unit) were divided randomly into the following groups: "control", "sham", "vehicle", "GPE", "IGF-I", and "NGF", depending on the treatment each animal was to undergo. "Control" animals were weighed at the first and last time points and were not treated or handled at any other time. "Sham" animals underwent a sham surgery of anesthesia, incision through the scalp skin, drill hole through the skull, bone wax to seal the drill hole, and sutures for the skin incision. They were then handled daily in mock infusions to mimic handling of animals that received lesions and intracerebroventricular infusions.

"Vehicle", "GPE", "IGF-I", and "NGF" animals were anaesthetized with 75 mg/Kg sodium pentobarbital and positioned in a stereotaxic apparatus (Kopf Instruments, USA), and underwent unilateral fimbria-fomix lesions to lesion septal cholinergic neurons and chronic cannula implantation into the left lateral cerebral ventricle. Fomix-fimbria lesions were performed by transecting the fimbria-fornix projection using a specialized retractable wire Scouten knife (Kopf Instruments) designed to minimize tissue damage except at the required lesion site. Anaesthetized animals received an incision through their scalp skin and a small drill hole was made in the skull at the stereotaxic coordinates anterior-posterior (AP) axis–1.0 mm from the bregma and medial-lateral (ML) axis+2.5 mm from midline (left side), from an atlas of the rat brain (Paxinos et al. (1986), "The rat brain in stereotaxic coordinates", Academic Press, London). The knife was lowered into the brain through the drill hole to the coordinate+6.0 mm ventral to the skull on the dorsal-ventral (DV) axis. The knife blade was then extended 2.5 mm toward midline at an angle of 30° caudal to the bregma. The knife, with blade extended, was then raised 4.5 mm dorsally to axotomize the fimbria-fomix fibres. The blade was then retracted, the knife lowered 4.5 mm to its original coordinate, and the process was repeated. The blade was then retracted and the knife was withdrawn. Bone wax was used to seal up the drill hole. A permanent 22-gauge metal guide cannula was then fixed into place in the left lateral cerebral ventricle at coordinates–2.5 mm AP, 1.9 mm ML, and–4.0 mm DV. Dental cement was used to permanently fix the guide cannula into place. A temporary dummy internal cannula was placed into the guide cannula to close it off. Sutures were then used to close the skin incision.

"Vehicle", "GPE", "IGF-I", and "NGF" animals received daily infusions (at about the same time every day) of their respective compounds. The vehicle consisted of phosphate buffered saline (PBS) with 0.1% bovine serum albumin (BSA), pH 7.4, filter-sterilized. GPE and NGF powder were made up using this vehicle, with GPE having a concentration of 1.5 mg/mL and NGF having a concentration of 0.5 mg/mL. The concentration of IGF-I was 10 mg/mL. Animals received intracerebroventricular infusions of 2 µL daily; thus "vehicle" animals received 2 µL/day of vehicle, "GPE" animals received 3 µg/day GPE in 2 µL vehicle (approximately 15 µg/Kg/day of GPE), "IGF-1" animals received 20 µg/day IGF-I in 2 µL vehicle (approximately 100 µg/Kg/day of IGF-I), and "NGF" animals received 1 µg/day NGF in 2 µL vehicle (approximately 5 µg/Kg/day of NGF). Animals received their first infusion during the lesion/cannulation surgery, and then daily for 14 days. The infusions were performed using a 28-gauge internal cannula attached to a Hamilton syringe to deliver 2 µL volumes accurately. The temporary dummy cannula was removed, the internal cannula was fitted, the compound was delivered, and the dummy cannula was replaced. The internal cannula was sterilized with ethanol between animals. Each compound had a dedicated Hamilton syringe and internal cannula. The animals were weighed prior to anaesthesia for surgery using a standard laboratory scale, and were weighed again on day 14 before sacrifice.

The results are shown in the FIGURE, where the numbers above the bars represent the average weight increase in grams over the 14 days. Control animals gained weight normally, and sham treated animals nearly as rapidly. Animals that underwent surgery (lesion/cannulation) and were administered only vehicle gained less weight. In the NGF-treated lesioned group there was no weight gain; and in the IGF-I-treated lesioned group there was minimal weight gain. By contrast, in the GPE-treated lesioned group, the normally expected weight gain occurred, a result that is significantly different from the vehicle-treated lesioned group. GPE restores the rate of weight gain to normal levels following a neurosurgical trauma that leads to weight loss in animals not receiving GPE.

EXAMPLE 2

GPE in a dose of 10 µg/Kg/day is administered via lateral cerebroventricular injection into the brain of a human patient suffering from a head injury to promote weight gain to normal levels. Alternatively, a GPE analog is administered. Treatment is commenced as soon as possible after the head injury and then for 14 days thereafter. Normal weight gain is promoted in the patient.

EXAMPLE 3

A GPE analog in a dose of 20 µg/Kg/day is administered via focal injection into the lateral cerebral ventricle of a human patient suffering from a head injury to promote weight gain to normal levels. Alternatively, GPE is administered. Treatment is commenced as soon as possible after the head injury and then for 14 days thereafter. Normal weight gain is promoted in the patient.

EXAMPLE 4

GPE in a dose of 5 µg/Kg/day is administered via a surgically inserted shunt into the lateral cerebral ventricle of a human patient suffering from a head injury to promote weight gain to normal levels. Alternatively, a GPE analog is administered. Treatment is commenced as soon as possible after the head injury and then for 14 days thereafter. Normal weight gain is promoted in the patient.

The disclosures of the documents referred to in this application are incorporated by reference into this application.

It will be appreciated by those persons skilled in the art that the above description is provided by way of an example only and that numerous changes and variations can be made without departing from the scope of the invention. All such changes and variations are intended to be within the scope of the following claims and their equivalents.

We claim:

1. A method of promoting weight gain in a mammal having a condition that leads to decreased weight gain or weight loss, comprising increasing the effective concentration of a GPE-related compound in the central nervous system.

2. The method of claim 1 where the GPE-related compound is GPE.

3. The method of claim 1 where the GPE-related compound is a GPE analog.

4. The method of claim 2 where the GPE analog is selected from the group consisting of GP, PE, GP(E-amide), GPE stearate, GP(D-E), GPT, GEP, EGP, and EPG.

5. The method of claim 1 where the condition is a neural injury.

6. The method of claim 5 where the neural injury is an acute brain injury.

7. The method of claim 6 where the acute brain injury is traumatic brain injury.

8. The method of claim 6 where the acute brain injury is a closed head injury.

9. The method of claim 6 where the acute brain injury is stroke.

10. The method of claim 1 where the condition is a neurological disease.

11. The method of claim 10 where the neurological disease is a chronic neurodegenerative disease.

12. The method of claim 11 where the neurodegenerative disease is Alzheimer's disease.

13. The method of claim 12 where the neurodegenerative disease is Parkinson's disease.

14. The method of claim 12 where the neurodegenerative disease is Huntington's disease.

15. The method of claim 1 where the conditions is selected from severe burns, severe trauma, a chronic non-neurological disease, a chronic infection, and chronic corticosteroid administration.

16. The method of claim 1 where the condition is AIDS.

17. The method of claim 1 comprising administration to the mammal of an effective amount of a GPE-related compound, a prodrug thereof, or an implant containing cells that express the GPE-related compound or prodrug.

18. The method of claim 17 where the GPE-related compound, prodrug, or implant is administered directly to the cerebral ventricle of the mammal.

19. The method of claim 17 where the GPE-related compound, prodrug, or implant is administered peripherally to the mammal.

20. The method of claim 17 where the condition is a neural injury and the GPE-related compound, prodrug or implant is first administered in the period from the time of the neural injury to 100 hours after injury, and then daily for 14 days.

21. The method of claim 20 where the GPE-related compound, prodrug, or implant is first administered in the period from the time of the neural injury to 8 hours after injury, and then daily for 14 days.

22. The method of claim 17 where the GPE-related compound is administered centrally in an amount from about 0.1 $\mu$g/Kg/day to about 400 $\mu$g/Kg/day.

23. The method of claim 22 where the GPE-related compound is administered centrally in an amount from about 0.5 $\mu$g/Kg/day to about 100 $\mu$g/Kg/day.

24. The method of claim 23 where the GPE-related compound is administered centrally in an amount from about 1 $\mu$g/Kg/day to about 25 $\mu$g/Kg/day.

* * * * *